United States Patent
Leanna et al.

(10) Patent No.: US 10,898,354 B2
(45) Date of Patent: Jan. 26, 2021

(54) TRACHEAL STENT

(71) Applicant: BOSTON SCIENTIFIC SCIMED, INC., Maple Grove, MN (US)

(72) Inventors: Gary J. Leanna, Holden, MA (US); Dane T. Seddon, Boston, MA (US); Jason Weiner, Grafton, MA (US); Seamus F. O'Shaughnessy, Chelmsford, MA (US); Sean P. Fleury, Brighton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/268,659

(22) Filed: Feb. 6, 2019

(65) Prior Publication Data

US 2019/0175371 A1 Jun. 13, 2019

Related U.S. Application Data

(63) Continuation of application No. 14/932,407, filed on Nov. 4, 2015, now abandoned.
(Continued)

(51) Int. Cl.
*A61F 2/07* (2013.01)
*A61F 2/04* (2013.01)
*A61F 2/89* (2013.01)
*A61F 2/915* (2013.01)
*A61F 2/844* (2013.01)

(52) U.S. Cl.
CPC .............. *A61F 2/89* (2013.01); *A61F 2/04* (2013.01); *A61F 2/07* (2013.01); *A61F 2/844* (2013.01); *A61F 2/915* (2013.01); *A61F 2002/043* (2013.01); *A61F 2002/046* (2013.01); *A61F 2002/91558* (2013.01); *A61F 2002/91566* (2013.01); *A61F 2002/91575* (2013.01); *A61F 2002/91583* (2013.01); *A61F 2210/0004* (2013.01); *A61F 2210/0014* (2013.01); *A61F 2220/0008* (2013.01)

(58) Field of Classification Search
CPC .................................................. A61F 2002/046
See application file for complete search history.

(56) References Cited

U.S. PATENT DOCUMENTS

| | | | |
|---|---|---|---|
| 4,994,071 A | 2/1991 | MacGregor | |
| 5,591,197 A | 1/1997 | Orth et al. | |
| (Continued) | | | |

FOREIGN PATENT DOCUMENTS

| | | |
|---|---|---|
| EP | 0732088 A2 | 9/1996 |
| WO | 199733532 A2 | 9/1997 |
| (Continued) | | |

*Primary Examiner* — Jacqueline Woznicki
(74) *Attorney, Agent, or Firm* — Seager, Tufte & Wickhem, LLP

(57) ABSTRACT

Tracheal stents may include a plurality of wave form structures each extending radially about the support structure, a plurality of axial loop members extending axially between adjacent wave form structures and a polymeric covering disposed thereover. Tracheal stents may include an expandable metal structure and a plurality of spacer fins extending above an outer surface of the expandable metal structure. The plurality of spacer fins may be formed of a material different than that of the expandable metal structure.

15 Claims, 8 Drawing Sheets

Related U.S. Application Data

(60) Provisional application No. 62/076,181, filed on Nov. 6, 2014.

(56) References Cited

U.S. PATENT DOCUMENTS

| | | | |
|---|---|---|---|
| 5,609,627 A * | 3/1997 | Goicoechea | A61F 2/82 128/898 |
| 5,674,277 A | 10/1997 | Freitag | |
| 5,681,346 A | 10/1997 | Orth et al. | |
| 5,800,526 A | 9/1998 | Anderson et al. | |
| 5,814,063 A | 9/1998 | Freitag | |
| 6,210,429 B1 | 4/2001 | Vardi et al. | |
| 7,527,644 B2 | 5/2009 | Mangiardi et al. | |
| 7,547,321 B2 | 6/2009 | Silvestri et al. | |
| 7,604,660 B2 | 10/2009 | Borg et al. | |
| 7,608,099 B2 | 10/2009 | Johnson et al. | |
| 7,637,934 B2 | 12/2009 | Mangiardi et al. | |
| 7,637,942 B2 | 12/2009 | Mangiardi et al. | |
| 7,651,520 B2 | 1/2010 | Fischell et al. | |
| 7,731,654 B2 | 6/2010 | Mangiardi et al. | |
| 7,785,360 B2 | 8/2010 | Freitag | |
| 7,803,180 B2 | 9/2010 | Burpee et al. | |
| 7,806,918 B2 | 10/2010 | Nissl et al. | |
| 7,875,068 B2 | 1/2011 | Mangiardi et al. | |
| 7,887,579 B2 | 2/2011 | Mangiardi et al. | |
| 7,942,921 B2 | 5/2011 | Nissl et al. | |
| 7,959,671 B2 | 6/2011 | Mangiardi et al. | |
| 8,080,053 B2 | 12/2011 | Satasiya et al. | |
| 8,092,549 B2 | 1/2012 | Hillis et al. | |
| 8,128,679 B2 | 3/2012 | Casey | |
| 8,142,488 B2 | 3/2012 | Reynolds et al. | |
| 8,197,529 B2 | 6/2012 | Cully et al. | |
| 8,206,436 B2 | 6/2012 | Mangiardi et al. | |
| 8,262,721 B2 | 9/2012 | Welborn et al. | |
| 8,267,987 B2 | 9/2012 | Johnson et al. | |
| 8,292,946 B2 | 10/2012 | Thistle et al. | |
| 8,298,277 B2 | 10/2012 | Mangiardi et al. | |
| 8,323,350 B2 | 12/2012 | Nissl | |
| 8,353,946 B2 | 1/2013 | Mangiardi et al. | |
| 8,444,688 B2 | 5/2013 | Sherry | |
| 8,535,366 B2 | 9/2013 | Mangiardi et al. | |
| 8,652,196 B2 | 2/2014 | Nissl | |
| 8,715,334 B2 | 5/2014 | Clerc et al. | |
| 8,834,558 B2 | 9/2014 | Nissl | |
| 8,926,683 B2 | 1/2015 | Gill et al. | |
| 2003/0176911 A1 * | 9/2003 | Iancea | A61F 2/915 623/1.13 |
| 2004/0117004 A1 | 6/2004 | Osborne et al. | |
| 2005/0131515 A1 | 6/2005 | Cully et al. | |
| 2007/0005127 A1 | 1/2007 | Boekstegers et al. | |
| 2007/0213810 A1 | 9/2007 | Newhauser et al. | |
| 2008/0249598 A1 | 10/2008 | Sherry | |
| 2009/0024813 A1 | 1/2009 | Bloom et al. | |
| 2009/0187240 A1 | 7/2009 | Clerc et al. | |
| 2010/0286760 A1 | 11/2010 | Beach et al. | |
| 2011/0230957 A1 | 9/2011 | Bonsignore et al. | |
| 2012/0150277 A1 | 6/2012 | Wood et al. | |
| 2012/0283811 A1 | 11/2012 | Neilan | |
| 2012/0310363 A1 | 12/2012 | Gill et al. | |
| 2013/0018215 A1 | 1/2013 | Snider et al. | |
| 2013/0018452 A1 | 1/2013 | Weitzner et al. | |
| 2013/0085565 A1 | 4/2013 | Eller et al. | |
| 2013/0103163 A1 | 4/2013 | Krimsky et al. | |
| 2013/0110253 A1 | 5/2013 | Gill et al. | |
| 2013/0116770 A1 | 5/2013 | Robinson | |
| 2013/0116771 A1 | 5/2013 | Robinson | |
| 2013/0116772 A1 | 5/2013 | Robinson | |
| 2013/0123897 A1 | 5/2013 | Robinson | |
| 2013/0138202 A1 * | 5/2013 | Paul | A61F 2/07 623/1.15 |
| 2013/0172983 A1 * | 7/2013 | Clerc | A61F 2/848 623/1.16 |
| 2013/0184808 A1 | 7/2013 | Hall et al. | |
| 2013/0184810 A1 | 7/2013 | Hall et al. | |
| 2013/0325141 A1 | 12/2013 | Gill et al. | |
| 2014/0067046 A1 | 3/2014 | Perry et al. | |
| 2014/0067047 A1 | 3/2014 | Eller et al. | |
| 2014/0079758 A1 | 3/2014 | Hall et al. | |
| 2014/0081414 A1 | 3/2014 | Hall et al. | |
| 2014/0086971 A1 | 3/2014 | Hall et al. | |
| 2014/0248418 A1 | 9/2014 | Eller et al. | |
| 2014/0249619 A1 | 9/2014 | Eller et al. | |
| 2014/0257461 A1 | 9/2014 | Robinson et al. | |
| 2014/0277442 A1 * | 9/2014 | Seddon | A61F 2/848 623/9 |
| 2014/0277562 A1 | 9/2014 | Seddon et al. | |
| 2014/0277573 A1 | 9/2014 | Gill et al. | |
| 2015/0073529 A1 | 3/2015 | Fleury et al. | |
| 2015/0148887 A1 | 5/2015 | Beach et al. | |
| 2015/0157475 A1 * | 6/2015 | Consigny | A61F 2/94 623/1.11 |
| 2018/0092732 A1 * | 4/2018 | Kringle | A61F 2/07 |
| 2018/0125682 A1 * | 5/2018 | Folan | A61F 2/04 |

FOREIGN PATENT DOCUMENTS

| | | |
|---|---|---|
| WO | 2010124286 A1 | 10/2010 |
| WO | 2012047308 A1 | 4/2012 |
| WO | 2015038790 A1 | 3/2015 |

* cited by examiner

TRACHEAL STENT

CROSS-REFERENCE TO RELATED APPLICATIONS

This application is a continuation of U.S. application Ser. No. 14/932,407, filed Nov. 4, 2015, which claims priority under 35 U.S.C. § 119 to U.S. Provisional Application Ser. No. 62/076,181, filed Nov. 6, 2014, the entirety of which is incorporated herein by reference.

TECHNICAL FIELD

The present disclosure pertains to medical devices, and methods for manufacturing medical devices. More particularly, the present disclosure pertains to endoprostheses such as tracheal stents.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered stents, on the other hand, prevent tissue ingrowth to facilitate removal. However, fully covered endoprostheses are prone to migrate through the body lumen.

Accordingly, it is desirable to provide endoprostheses that exhibit anti-migration features, while reducing the trauma to the body lumen of the patient if removal of the endoprosthesis is desired.

BRIEF SUMMARY

The disclosure is directed to several alternative designs, materials and methods of manufacturing medical device structures and assemblies, and uses thereof.

In one example, a medical stent, such as a tracheal stent, extends from a first end to a second end and includes a support structure extending from the first end to the second end. The support structure includes a plurality of wave form structures each extending circumferentially about the support structure and a plurality of axial loop members extending axially between adjacent wave form structures and a polymeric covering disposed over the support structure. At least some of the plurality of axial loop members are configured to include an extended configuration in which the at least some of the plurality of axial loop members extend radially outward from an outer surface defined by the plurality of wave form structures.

Alternatively, or additionally, at least some of the wave form structures extend circumferentially about 360 degrees about the support structure and form closed rings.

Alternatively, or additionally, at least some of the wave form structures include a nickel-titanium alloy.

Alternatively, or additionally, at least some of the wave form structures are formed from nitinol wire.

Alternatively, or additionally, at least some of the wave structures are defined by a wire diameter that is in the range of about 0.2 millimeters (mm) to about 0.5 mm. Alternatively, or additionally, at least some of the wave form structures are defined by a wave frequency in the range of about 0.5 to about 4 waves per centimeter (cm) and a wave amplitude in the range of about 0.25 cm to about 1 cm.

Alternatively, or additionally, at least some of the plurality of axial loop members extend from a peak, a valley or a transition region of a wave form structure of the plurality of wave form structures to a peak, a valley or a transition region of an adjacent wave form structure of the plurality of wave form structures.

Alternatively, or additionally, the plurality of axial loop members provide the only direct connection between adjacent wave form structures of the plurality of wave form structures.

In another example, a support structure for an endoprosthesis has a first end, a second end and a lumen extending therebetween. The support structure includes a first wave form structure extending circumferentially about the support structure and defining a first closed ring, the first wave form structure formed of a first wire oscillating in a wave form having a first wave frequency and a first wave amplitude. The support structure includes a second wave form structure extending circumferentially about the support structure and defining a second closed ring, the second wave form structure formed of a second wire oscillating in a wave form having a second wave frequency and a second wave amplitude. An axial loop member extends from the first wave form structure to the second wave form structure and provides a connection between the first wave form structure and the second wave form structure and is configured to include an extended configuration in which the axial loop member extends radially outward from an outer surface defined by the first and second wave form structures.

Alternatively, or additionally, the first wave form structure and the second wave form structure are formed from nitinol wire.

Alternatively, or additionally, at least some of the wave structures are defined by a wire diameter that is in the range of about 0.2 mm to about 0.5 mm.

Alternatively, or additionally, at least some of the wave form structures are defined by a wave frequency in the range of about 0.5 to about 4 waves per cm and a wave amplitude in the range of about 0.25 cm to about 1 cm.

Alternatively, or additionally, in another example, the axial loop member extends from a peak, a valley or a transition region of the first wave form structure to a peak, a valley or a transition region of the second wave form structure.

In another example, a method of forming a support structure for an endoprosthesis having a first end, a second end and a lumen extending therebetween includes forming a first wave form structure from a first wire, the first wave form structure undulating side to side while extending circumferentially around to form a first closed ring. A second wave form structure is formed from a second wire, the second wave form structure undulating side to side while extending circumferentially around to form a second closed ring. An axial loop member having a first end and a second end is secured, the first end secured to the first wave form structure and the second end secured to the second wave form structure.

Alternatively, or additionally, the first wave form structure is formed on a mandrel.

Alternatively, or additionally, the second wave form structure is formed on a mandrel.

Alternatively, or additionally, the method further includes forming a plurality of additional wave form structures from a plurality of wires, each of the plurality of additional wave form structures undulating side to side while extending circumferentially around to form a plurality of additional closed rings.

Alternatively, or additionally, the method further includes securing a plurality of axial loop members between adjacent wave form structures of the plurality of additional wave form structures.

Alternatively, or additionally, the first wire and the second wire include a nitinol wire.

Alternatively, or additionally, the first end of the axial loop member is secured to the first wave form structure via welding.

In another example, a medical stent, such as a tracheal stent, extending from a distal end to a proximal end includes an expandable metal structure extending from the distal end to the proximal end, the expandable metal structure convertible between a compressed configuration for delivery and an expanded configuration once deployed, the expandable metal structure including an inner surface defining a stent lumen and an outer surface. A plurality of spacer fins extends above the outer surface of the expandable metal structure and are formed of a material different than that of the expandable metal structure.

Alternatively, or additionally, the plurality of spacer fins are formed of a biodegradable or bioabsorbable material.

Alternatively, or additionally, the plurality of spacer fins are formed from a filament that is interlaced within the expandable metal structure.

Alternatively, or additionally, the plurality of spacer fins are separately formed each having an end, and the ends of the plurality of spacer fins are encapsulated in a polymeric coating that is disposed over the expandable metal structure.

Alternatively, or additionally, the plurality of spacer fins include a cap secured to high spots formed within the expandable metal structure.

Alternatively, or additionally, at least some of the plurality of spacer fins are triangular in shape, with a base secured relative to the expandable metal structure and an apex extending above the base.

Alternatively, or additionally, the expandable metal structure comprises a laser cut expandable metal structure.

Alternatively, or additionally, the expandable metal structure includes a woven or braided expandable metal structure.

In another example, a medical stent, such as a tracheal stent, extending from a distal end to a proximal end includes an expandable metal structure extending from the distal end to the proximal end, the expandable metal structure convertible between a compressed configuration for delivery and an expanded configuration once deployed, the expandable metal structure including an inner surface defining a stent lumen and an outer surface. A biodegradable filament is interwoven through the expandable metal structure to form a plurality of biodegradable spacer fins extending above the outer surface of the expandable metal structure.

Alternatively, or additionally, the expandable metal structure includes a laser cut expandable metal structure.

Alternatively, or additionally, the expandable metal structure includes a woven or braided expandable metal structure.

Alternatively, or additionally, the biodegradable filament includes square or round shaped protruding caps.

Alternatively, or additionally, the biodegradable filament has a diameter in the range of about 0.1 cm to about 1 cm.

Alternatively, or additionally, at least some of the plurality of spacer fins are triangular in shape.

In another example, a medical stent, such as a tracheal stent, extending from a distal end to a proximal end includes an expandable metal structure extending from the distal end to the proximal end, the expandable metal structure convertible between a compressed configuration for delivery and an expanded configuration once deployed, the expandable metal structure including an inner surface defining a stent lumen and an outer surface. A polymeric coating is disposed over the expandable metal structure and a plurality of biodegradable spacer fins are secured relative to the polymeric coating, the plurality of biodegradable spacer fins extending above the outer surface of the expandable metal structure.

Alternatively, or additionally, at least some of the plurality of spacer fins are triangular in shape, with a base secured relative to the expandable metal structure and an apex extending above the base.

Alternatively, or additionally, the plurality of biodegradable spacer fins are separately formed each having an end, and the ends of the plurality of biodegradable spacer fins are encapsulated in the polymeric coating.

Alternatively, or additionally, the plurality of biodegradable spacer fins are formed of a biodegradable material comprising poly-1-lactide acid (PLLA) and/or poly(lactide-co-Glycoside 8515) (PLGA 8515).

Alternatively, or additionally, the plurality of biodegradable spacer fins have an average height, relative to the outer surface of the expandable metal structure, ranging from about 0.1 cm to about 0.5 cm.

Alternatively, or additionally, the polymeric coating includes silicone.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be further understood in consideration of the following detailed description in connection with the accompanying drawings, in which.

Figure 1:
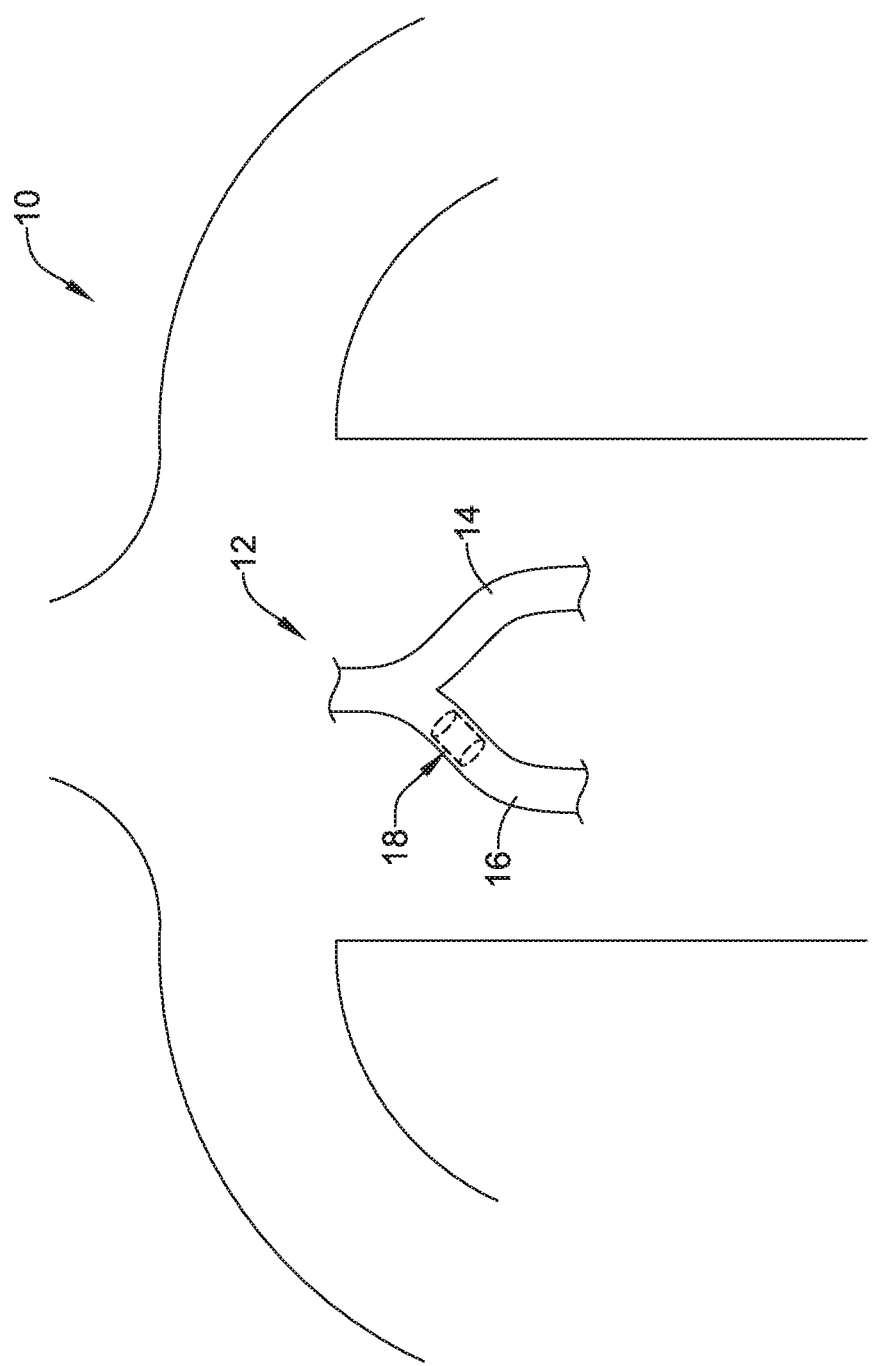
FIG. 1 is a schematic illustration of a patient, showing a trachea stent disposed within the patient's right main bronchus in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment. It will be appreciated that while the disclosure describes an airway or trachea stent, the features and elements described herein may be applied to any variety of endoprosthesis.

FIG. 1 provides a schematic illustration of the torso of a patient 10. The patient 10 includes a trachea 12, a left main bronchus 14 and a right main bronchus 16 (relative to the patient's perspective). An endoprosthesis 18 may be seen in phantom, disposed within the right main bronchus 16. It will be appreciated that this placement is merely for illustrative purposes, as the endoprosthesis 18 may be deployed elsewhere in the trachea 12 or even down into the bronchia (not illustrated). It will also be appreciated that while the endoprosthesis 18 is described herein as an airway stent, the endoprosthesis 18 may be deployed in a variety of other bodily lumens, including but not limited to the vascular, urinary, biliary, tracheobronchial, esophageal or renal tracts.

Although illustrated as a stent, the endoprosthesis 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

A difficulty in placing an endoprosthesis in the trachea 12 is that the patient 10 may have a tendency to try and cough out the endoprosthesis 18. The human respiratory system is designed, when encountering an obstacle or other foreign object, to try to move the obstacle out of the way. This may mean pushing the object farther down, to a position of relative safety. This may also mean trying to cough it out. The human body may try to forcibly eject the object. Accordingly, and in some embodiments, the endoprosthesis 18 may be configured to help hold the endoprosthesis 18 in place within the trachea 12.

Another difficulty in placing an endoprosthesis in the trachea 12 is that the presence of a foreign object such as an endoprosthesis triggers an inflammatory response that produces mucus. Mucus can become trapped between the body of an endoprosthesis and the wall of the trachea 12. Trapped mucus can stimulate or facilitate the growth of bacteria. Accordingly, and in some embodiments, the endoprosthesis 18 may be configured to provide air channels or voids by spacing at least a part of the endoprosthesis 18 away from the wall of the trachea 12.

Figure 2:
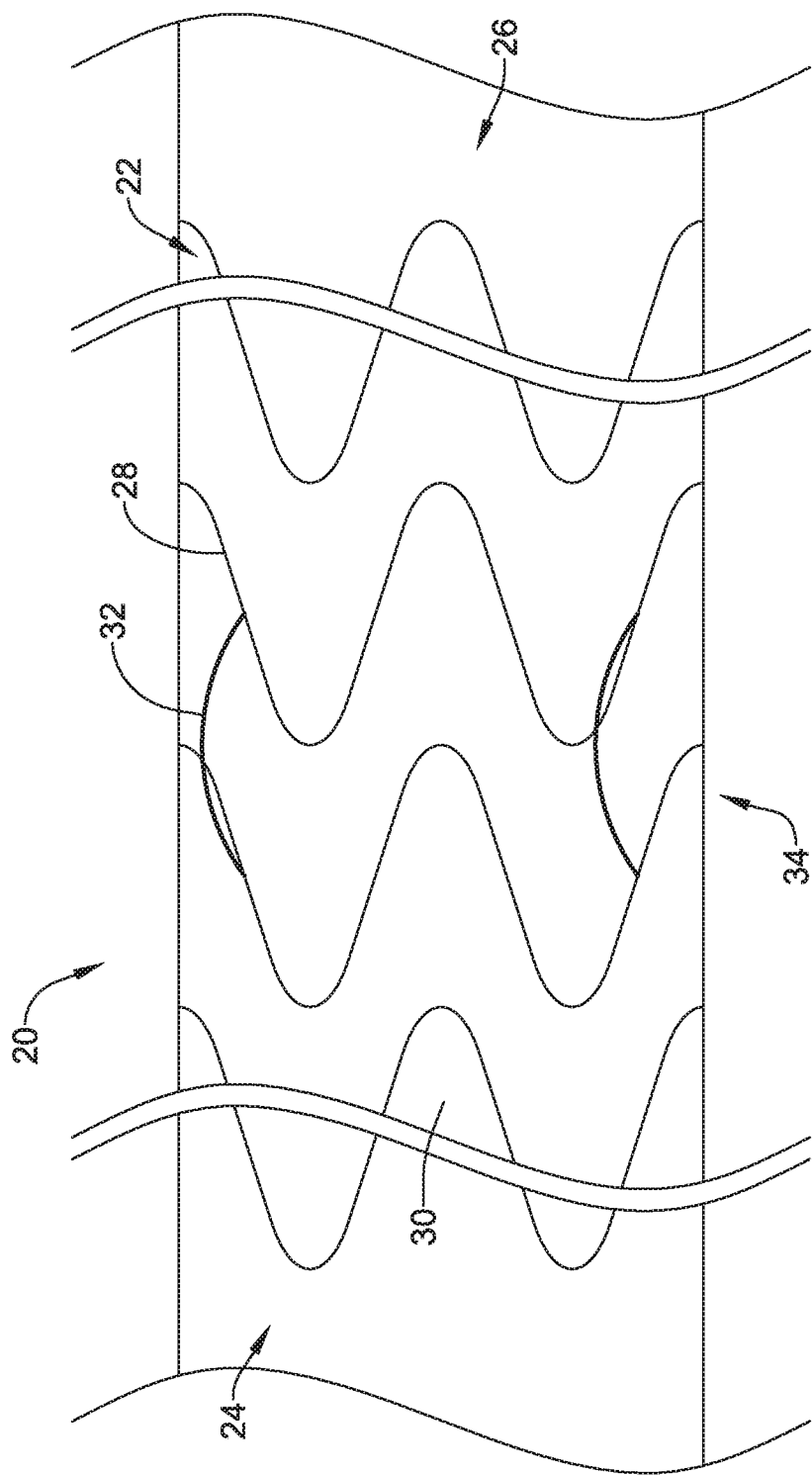
FIG. 2 is an illustration of a trachea stent in accordance with an embodiment of the disclosure.

FIG. 2 provides an illustration of a trachea stent 20 that may be deployed as shown with respect to the endoprosthesis 18 of FIG. 1. In FIG. 2, the trachea stent 20 is shown on a mandrel 30. The trachea stent 20 may include a support structure 22 extending from a first end 24 to a second end 26. The support structure 22 may include one or more (a plurality are illustrated) wave form structures 28 that extend circumferentially about the support structure 22. In some embodiments, the wave form structures 28 extend about 360 degrees about the support structure 22 and thus each of the wave form structures 28 may form closed loops. In some embodiments, each wave form structure 28 is formed independently of any other wave form structure 28. The wave form structures 28 may be arranged axially adjacent one another along the length of the support structure 22. In some embodiments, each wave form structure 28 may be formed on the mandrel 30, by forming a wire into the sinusoidal pattern shown, having peaks oriented toward the first end 24 of the support structure 22 and valleys oriented toward the second end 26 of the support structure 22.

The wave form structures 28 are joined together via connectors, such as one or more axial loop members 32. In some embodiments, the axial loop members 32 (two are illustrated in FIG. 2) are the only physical connection between adjacent wave form structures 28. It will be appreciated that, while not illustrated, the trachea stent 20 may include a polymeric coating or covering to prevent tissue ingrowth into the interior of the trachea stent 20. The polymeric coating or covering, if present, may be disposed about an exterior of the support structure 22, for example. The axial loop members 32 are shown in an extended configuration in which they extend radially outward from an outer surface 34 that is defined by the wave form structures 28 and the polymeric coating or covering, if present. While not illustrated, it will be appreciated that the support structure 22 may have a compressed configuration for delivery in which the axial loop members 32 flatten against the outer surface 34.

The connectors or axial loop members 32 may be configured to engage a wall of a body lumen in the expanded state to inhibit migration of the endoprosthesis 18 subsequent to implanting the endoprosthesis 18 in the body lumen. For example, the connectors or axial loop members 32 may engage the tissue between cartilage rings within the tracheal anatomy to provide anti-migration support for the endoprosthesis 18.

A space or opening may be defined between the connectors or axial loop member 32 and the outer circumference of the wave form structures 28 and/or overlaying polymeric coating or covering as viewed along the central longitudinal axis of the support structure 22, as a result of the connectors or axial loop members 32 extending radially outward of or above the outer circumference of the wave form structures 28 and/or overlaying polymeric coating or covering. The space or opening may be unobstructed by any other structure of the endoprosthesis 18. Accordingly, tissue ingrowth through these spaces or openings subsequent to implanting the endoprosthesis 18 may further secure the endoprosthesis 18 in place in the anatomy and prevent migration of the endoprosthesis 18.

The support structure 22 may be formed of any suitable material. In some embodiments, the support structure 22 may be formed of a nickel-titanium alloy such as nitinol. In some embodiments, at least some of the wave form structures 28 may be formed of a nitinol or other wire having a wire diameter that is in the range of about 0.2 mm to about 0.5 mm. In some embodiments, at least some of the axial loop members 32 may be formed of a nitinol or other wire having a wire diameter that is in the range of about 0.25 mm to about 0.4 mm, which may be the same or different from the wire diameter used to form at least some of the wave form structures 28.

Figure 3:
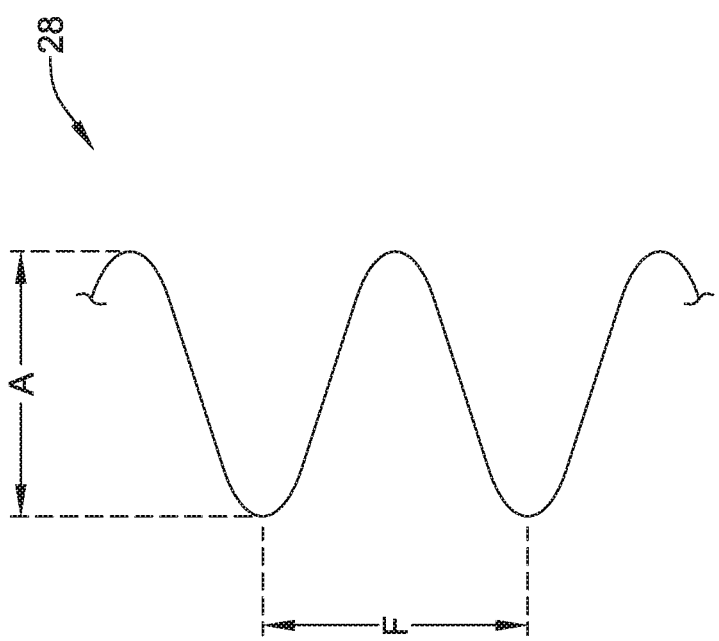
FIG. 3 is a schematic illustration of a portion of the trachea stent of FIG. 2 in accordance with an embodiment of the disclosure.

FIG. 3 provides an illustration of a portion of a wave form structure 28. In some embodiments, at least some of the wave form structures 28 may be considered as undulating back and forth in a sinusoidal pattern. A sinusoidal pattern may be defined, at least in part, by a frequency and an amplitude. As illustrated, the wave form structure 28 may be considered as having a frequency that is in the range of about 0.5 to about 4 waves per cm. A wave may be defined as the distance or wavelength F between adjacent peaks. The wave form structure 28 may be considered as having an amplitude A, measured as the distance between peak and valley. In this, it will be appreciated that peaks and valleys are a matter of perspective. What appears as a peak from one side looks like a valley if viewing from the opposite side.

Figure 4:
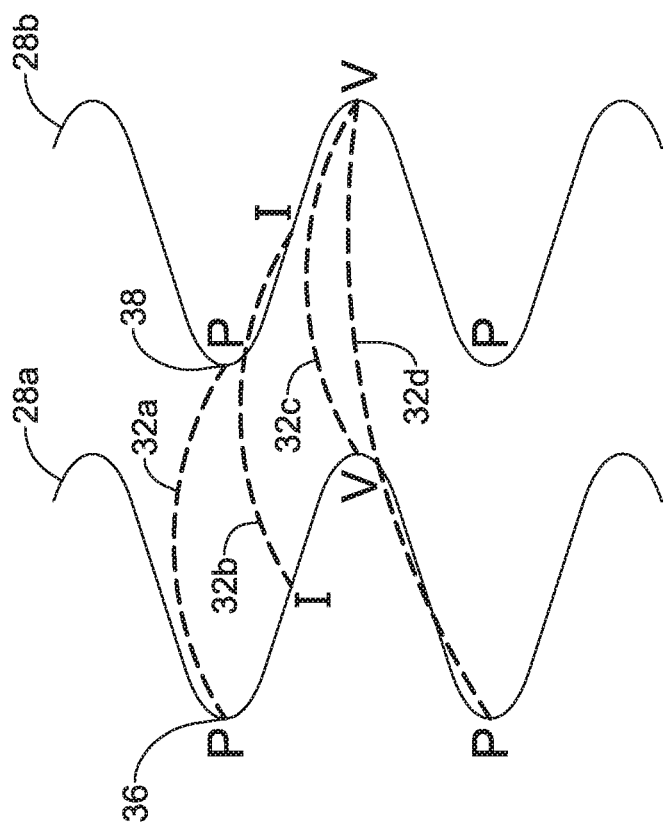
FIG. 4 is a schematic illustration of a portion of the trachea stent of FIG. 2 in accordance with an embodiment of the disclosure.

FIG. 4 provides an illustration of two adjacent wave form structures 28. One of the wave form structures (i.e., the first wave form structure) is labeled as 28a and the adjacent wave form structure (i.e., the second wave form structure) is labeled as 28b. To avoid confusion, each wave form structure 28a, 28b are labeled as having peaks P and valleys V. It will be appreciated that in connecting the axial loop members 32 to adjacent wave form structures 28, there are a variety of different relative locations at which the axial loop members 32 may be connected. Each axial loop member 32 may be considered as having a first end 36 connected to the first wave form structure 28a and a second end 38 connected to the adjacent second wave form structure 28b.

In FIG. 4, an axial loop member 32a is shown having its first end 36 secured to a peak P on the wave form structure 28a and its second end 38 secured to a peak P on the wave form structure 28b. An axial loop member 32b is shown extending from an intermediate position I on the wave form structure 28a to an intermediate position I on the wave form structure 28b. An axial loop member 32c is shown extending from a valley V on the wave form structure 28a to a valley V on the wave form structure 28b. An axial loop member 32d is shown extending from a peak P on the wave form structure 28a to a valley V on the wave form structure 28b. It will be appreciated that these axial loop members 32a, 32b, 32c and 32d, are illustrative only, and are intended merely to illustrate the variety of available connection points. In alternative embodiments, the first end 36 of the axial loop member 32 may be secured at any desired location along the first wave form structure 28a while the second end 38 of the axial loop member 32 may be secured at any desired location along the second wave form structure 28b.

Figure 5:
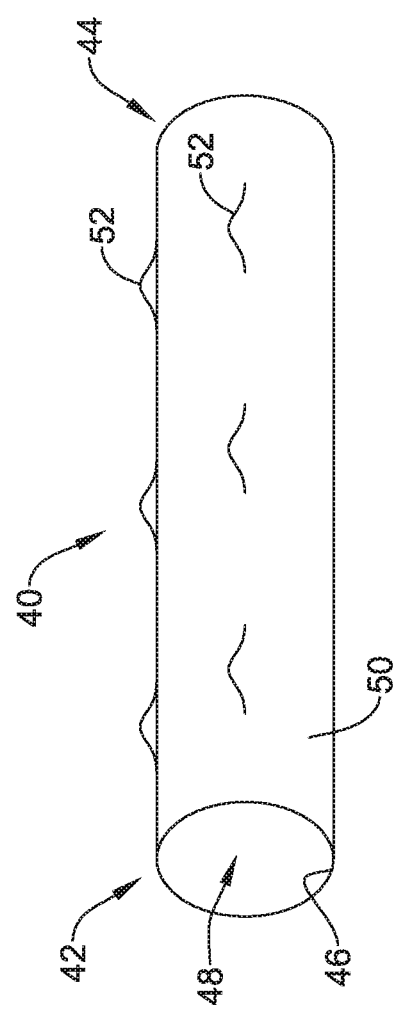
FIG. 5 is a perspective illustration of a trachea stent in accordance with an embodiment of the disclosure.

FIG. 5 provides a perspective illustration of a trachea stent 40 having a first end 42 and a second end 44. The trachea stent 40 has an inner surface 46 defining a lumen 48 and an outer surface 50. In some embodiments, as illustrated, the outer surface 50 includes a plurality of spacer fins 52 that extend above the outer surface 50. In some embodiments, the spacer fins 52 are formed of a different material. In some embodiments, the spacer fins 52 are formed of a biodegradable or bioabsorbable material that will break down or dissolve over time once implanted. Accordingly, the spacer fins 52 may provide migration resistance upon implantation of the trachea stent 40 within a body lumen. Over time, the spacer fins 52, which are formed of a biodegradable or bioabsorbable material, will break down or dissolve once implanted. Thereafter, if it is desired to remove the trachea stent 40 at a later time, the degradation or absorption of the spacer fins 52 will reduce the trauma experienced by the patient in removing the trachea stent 40 from the body lumen.

Illustrative but non-limiting examples of suitable biodegradable or bioabsorbable materials include polymers, such as poly-L-lactide (PLLA), polyglycolide (PGA), polylactide (PLA), poly-D-lactide (PDLA), polycaprolactone, polydioxanone, polygluconate, polylactic acid-polyethylene oxide copolymers, modified cellulose, collagen, poly(hydroxybutyrate), polyanhydride, polyphosphoester, poly(amino acids), and combinations thereof.

In some embodiments, the spacer fins 52 could also provide drug elution. The terms "therapeutic agents," "drugs," "bioactive agents," "pharmaceuticals," "pharmaceutically active agents", and other related terms may be used interchangeably herein and include genetic therapeutic agents, non-genetic therapeutic agents, and cells. Therapeutic agents may be used singly or in combination. A wide range of therapeutic agent loadings can be used in conjunction with the devices of the present invention, with the pharmaceutically effective amount being readily determined by those of ordinary skill in the art and ultimately depending, for example, upon the condition to be treated, the nature of the therapeutic agent itself, the tissue into which the dosage form is introduced, and so forth.

Some specific beneficial agents include anti-thrombotic agents, anti-proliferative agents, anti-inflammatory agents, anti-migratory agents, agents affecting extracellular matrix production and organization, antineoplastic agents, antimitotic agents, anesthetic agents, anti-coagulants, vascular cell growth promoters, vascular cell growth inhibitors, cholesterol-lowering agents, vasodilating agents, and agents that interfere with endogenous vasoactive mechanisms.

More specific drugs or therapeutic agents include paclitaxel, sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, and Serca 2 gene/protein, resiquimod, imiquimod (as well as other imidazoquinoline immune response modifiers), human apolioproteins (e.g., AI, AII, AIII, AIV, AV, etc.), vascular endothelial growth factors (e.g., VEGF-2), as well as derivatives of the forgoing, among many others.

Numerous additional therapeutic agents useful for the practice of the present invention may be selected from those described in paragraphs [0040] to [0046] of commonly assigned U.S. Patent Application Pub. No. 2003/0236514, the entire disclosure of which is hereby incorporated by reference.

While the spacer fins 52 are illustrated as being generally aligned along an axial length of the trachea stent 40 (i.e., generally parallel to a central longitudinal axis of the trachea stent 40), it will be appreciated that in some embodiments, the spacer fins 52 could be aligned perpendicular or at an acute angle relative to an axial length of the trachea stent 40 (i.e., generally non-parallel to a central longitudinal axis of the trachea stent 40, such as perpendicular to or at an acute angle to the central longitudinal axis of the trachea stent 40), in order to limit migration in a particular direction, for example. Moreover, while the spacer fins 52 are shown as being generally triangular in shape, it will be appreciated that in some cases the spacer fins 52 may have other shapes, such as round or square.

Figure 6:
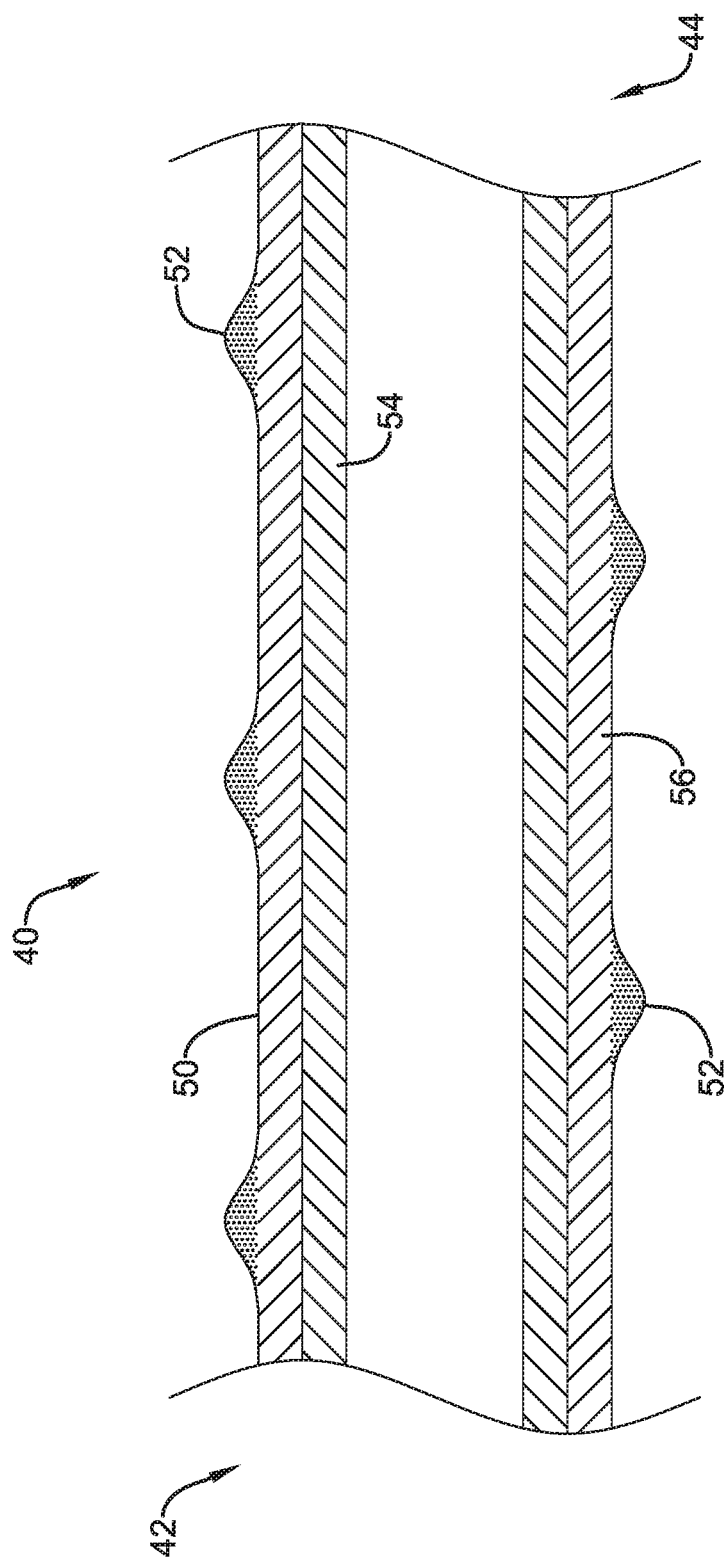
FIG. 6 is a schematic cross-sectional illustration of the trachea stent of FIG. 5 in accordance with an embodiment of the disclosure.

FIG. 6 provides a schematic cross-sectional view of the trachea stent 40, illustrating that the trachea stent 40 may, in some embodiments, include an expandable metal structure 54 and a polymeric coating or sleeve 56 disposed over the expandable metal structure 54. The expandable metal structure 54 is generically illustrated, as the expandable metal structure 54 may have any desired design and configuration. For example, in some embodiments, the expandable metal structure 54 may represent a laser cut structure that can be laser cut from a tube. In some embodiments, the expandable metal structure 54 may represent a wound metal structure. In some embodiments, the expandable metal structure 54 may represent a braided metal structure. In some embodiments, as shown in FIG. 6, the spacer fins 52 may be secured relative to the trachea stent 40 by encapsulating the spacer fins 52 within the polymeric coating or sleeve 56. In some embodiments, the spacer fins 52 may have a base and an opposing apex positioned radially outward from the base, and the base of each of the spacer fins 52 may be encapsulated within the polymeric coating or sleeve 56 and the apex of each of the spacer fins is exposed from and extends radially outward from the polymeric coating or sleeve 56 such that the biodegradable material forming the spacer fins 52 are exposed after implantation.

Figure 7:
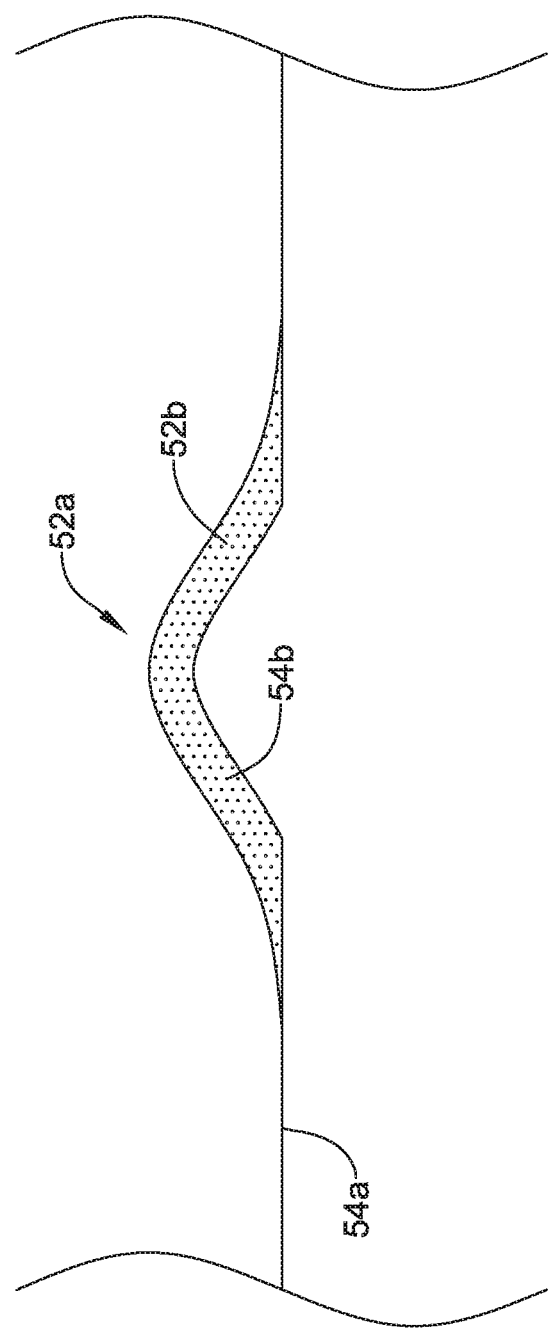
FIG. 7 is a schematic illustration of a portion of a trachea stent in accordance with an embodiment of the disclosure.

In some embodiments, the spacer fins 52 may be formed by placing a biodegradable cap directly on a portion of the expandable metal structure 54. As schematically illustrated in FIG. 7, an expandable metal structure 54a may include high spots 54b, such as an apex of a stent strut. A spacer fin 52a may be formed by securing a biodegradable cap 52b onto the high spot 54b or protruding portion of the expandable metal structure 54a. In some embodiments, while not illustrated, a polymeric covering or sleeve could cover the expandable metal structure 54a prior to securing the biodegradable cap 52b onto the high spot 54b or protruding portion.

Figure 8:
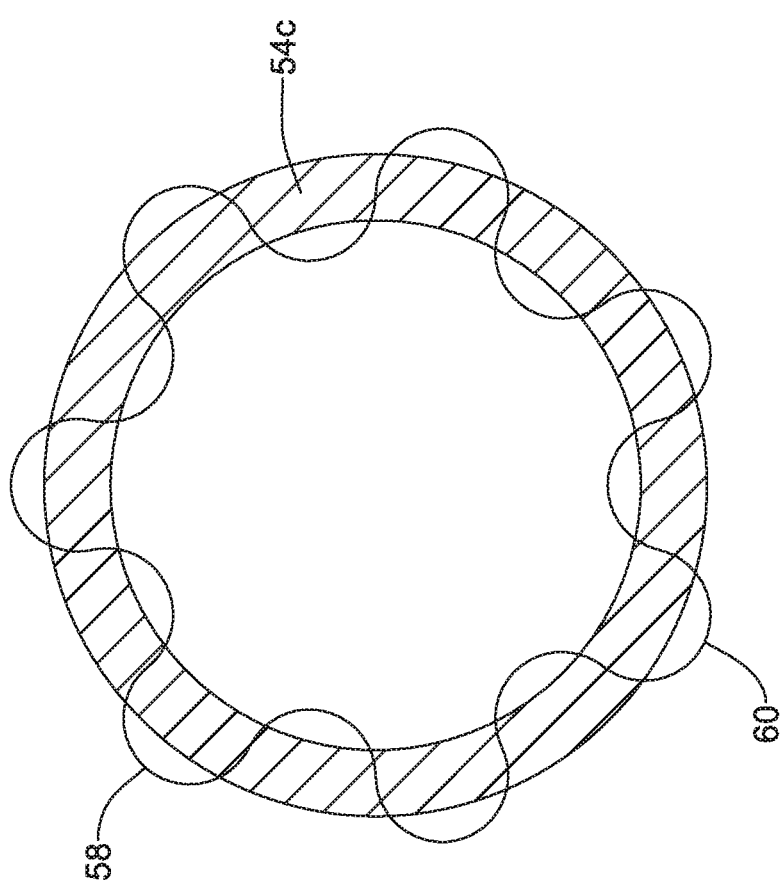
FIG. 8 is a schematic cross-sectional illustration of a portion of a trachea stent in accordance with an embodiment of the disclosure.

Another method for creating the spacer fins 52 is illustrated in FIG. 8, which shows a schematic cross-sectional view of an expandable metal structure 54c. As discussed above with respect to the expandable metal structure 54, the expandable metal structure 54c may generically represent a laser cut structure, a wound structure or a braided metal structure. A filament 58 may be wrapped around the expandable metal structure 54c, in and out of apertures formed within the expandable metal structure 54c such that the filament 58 forms high spots 60 or radially outwardly protruding portions. The high spots 60 or protruding portions may form spacer fins. While a single filament 58 is shown, it will be appreciated that a plurality of filaments 58 may be wrapped around the expandable metal structure 54c. The filament 58 may be formed of any desired biodegradable or bioabsorbable material, as discussed above with respect to the spacer fins 52, and may have any desired diameter such as about 0.5 cm.

In some embodiments, as noted, the expandable metal structure 54, 54b and 54c may be cut from a metal tube using any desired technique, including but not limited to micro-machining, saw-cutting (e.g., using a diamond grit embedded semiconductor dicing blade), electron discharge machining, grinding, milling, casting, molding, chemically etching or treating, or other known methods, and the like. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference.

In at least some embodiments, a laser cutting process may be used. The laser cutting process may include a suitable laser and/or laser cutting apparatus. For example, the laser cutting process may utilize a fiber laser. Utilizing processes like laser cutting may be desirable for a number of reasons. For example, laser cutting processes may allow for a number of different cutting patterns in a precisely controlled manner. Furthermore, changes to the cutting pattern can be made without the need to replace the cutting instrument (e.g., blade).

The materials that can be used for the expandable metal structure 54, 54b, 54c may include those commonly associated with medical devices. For simplicity purposes, the following discussion makes reference to the expandable metal structure 54. However, this is not intended to limit the devices and methods described herein, as the discussion may be applied to other similar structures.

The expandable metal structure 54, 54b, 54c, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS:

R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the trachea stents 20 and 40 described herein may also be doped with, made of, or otherwise include a radiopaque material. Radiopaque materials are understood to be materials capable of producing a relatively bright image on a fluoroscopy screen or another imaging technique during a medical procedure. Some examples of radiopaque materials can include, but are not limited to, gold, platinum, palladium, tantalum, tungsten alloy, polymer material loaded with a radiopaque filler, and the like.

In some embodiments, a degree of Magnetic Resonance Imaging (MRI) compatibility is imparted into the trachea stents 20, 40. For example, the trachea stents 20, 40, or portions thereof, may be made of a material that does not substantially distort the image and create substantial artifacts (e.g., gaps in the image). Certain ferromagnetic materials, for example, may not be suitable because they may create artifacts in an MRI image. Trachea stents 20, 40, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

As noted, the trachea stents 20, 40 may include a sheath or covering thereover. Suitable polymeric material include but are not limited to polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In some embodiments, the exterior surfaces of the expandable metal structures 22, 52 may be sandblasted, beadblasted, sodium bicarbonate-blasted, electropolished, etc. In these as well as in some other embodiments, a coating, for example a lubricious, a hydrophilic, a protective, or other type of coating may be applied thereover portions. Alternatively, the expandable metal structures 22, 52 may include a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical stent extending from a first end to a second end, the medical stent comprising:
   a support structure defining a lumen extending from the first end of the medical stent to the second end of the medical stent, the support structure including a plurality of wave form structures each extending circumferentially about the lumen and a plurality of axial loop members extending axially across a gap defined between adjacent wave form structures; and
   a polymeric covering disposed over the support structure and spanning at least the adjacent wave form structures and the gap defined therebetween, the polymeric covering being configured to prevent tissue ingrowth into the lumen;
   wherein at least some of the plurality of axial loop members are configured to include an extended configuration in which the at least some of the plurality of axial loop members extend radially outward and above an outer surface defined by the polymeric covering.

2. The medical stent of claim 1, wherein at least some of the wave form structures extend circumferentially 360 degrees about the lumen and form closed rings.

3. The medical stent of claim 1, wherein at least some of the wave form structures are formed from nitinol wire.

4. The medical stent of claim 1, wherein at least some of the wave form structures are defined by a wire diameter that is in a range of 0.2 to 0.5 millimeters.

5. The medical stent of claim 1, wherein at least some of the wave form structures are defined by a wave frequency in a range of 0.5 to 4 waves per centimeter and a wave amplitude in a range of 0.25 to 1 centimeters.

6. The medical stent of claim 1, wherein at least some of the plurality of axial loop members extend from a peak, a valley or a transition region of a wave form structure of the plurality of wave form structures to a peak, a valley or a transition region of an adjacent wave form structure of the plurality of wave form structures.

7. The medical stent of claim 1, further comprising an opening defined underneath each of the axial loop members and above an outer surface of the polymeric covering, the opening configured to permit tissue ingrowth.

8. The medical stent of claim 1, wherein the plurality of axial loop members are secured to the adjacent wave form structures.

9. The medical stent of claim 1, wherein the plurality of axial loop members do not extend into the lumen.

10. The medical stent of claim 1, wherein the plurality of axial loop members do not extend axially past the adjacent wave form structures.

11. A medical stent extending from a first end to a second end, the medical stent comprising:
    a support structure defining a lumen extending from the first end of the medical stent to the second end of the medical stent, the support structure including:
      a plurality of wires extending around a circumference of the lumen in an undulating fashion to form a plurality of closed loop wave form structures having alternating peaks oriented toward the first end and valleys oriented toward the second end; and
      a plurality of axial loop members connected directly to adjacent closed loop wave form structures and extending axially across a gap defined between adjacent closed loop wave form structures; and
    a polymeric covering disposed over the plurality of closed loop wave form structures and extending continuously across the gap between the adjacent closed loop wave form structures and covering the adjacent closed loop wave form structures, the polymeric covering being configured to prevent tissue ingrowth into the lumen;
    wherein the plurality of axial loop members are configured to include an extended configuration in which the plurality of axial loop members extend radially outward and above an outer surface of the polymeric covering;
    wherein the plurality of axial loop members define an opening defined underneath each of the axial loop members and above the outer surface of the polymeric covering; and
    wherein the opening is configured to permit tissue ingrowth.

12. The medical stent of claim 11, wherein the plurality of wires have a wire diameter that is in a range of 0.2 to 0.5 millimeters.

13. The medical stent of claim 11, wherein at least some of the wave form structures are defined by a wave frequency in a range of 0.5 to 4 waves per centimeter and a wave amplitude in a range of 0.25 to 1 centimeters.

14. The medical stent of claim 11, wherein each of the plurality of axial loop members extend from a peak of one of the plurality of wave form structures to a peak of an axially adjacent wave form structure of the plurality of wave form structures.

15. The medical stent of claim 11, wherein each of the plurality of axial loop members extend from an intermediate position between adjacent peaks and valleys of one of the plurality of wave form structures to an intermediate position between adjacent peaks and valleys of an axially adjacent wave form structure of the plurality of wave form structures.

\* \* \* \* \*